United States Patent [19]

Sawyer

[11] 4,082,507

[45] * Apr. 4, 1978

[54] PROSTHESIS AND METHOD FOR MAKING THE SAME

[76] Inventor: Philip N. Sawyer, 7600 Ridge Blvd., Brooklyn, N.Y. 11209

[*] Notice: The portion of the term of this patent subsequent to Dec. 23, 1992, has been disclaimed.

[21] Appl. No.: 684,664

[22] Filed: May 10, 1976

[51] Int. Cl.² .............................................. A61F 1/24
[52] U.S. Cl. .......................................... 8/94.11; 3/1; 8/94.19 R; 8/94.33; 128/1 R
[58] Field of Search ............... 8/94.19 R, 94.33, 94.11; 3/1; 128/1 R

[56] References Cited

U.S. PATENT DOCUMENTS

| | | | |
|---|---|---|---|
| 2,900,644 | 8/1959 | Rosenberg | 3/1 |
| 3,927,422 | 12/1975 | Sawyer | 3/1 |
| 3,966,401 | 6/1976 | Hancock et al. | 8/94.11 |
| 3,988,728 | 11/1976 | Dardik | 3/1 |

Primary Examiner—John Kight, III
Attorney, Agent, or Firm—Posnack, Roberts & Cohen

[57] ABSTRACT

A method is provided for controlling thrombogenicity of a vascular graft prosthesis by controlling the surface charge of at least the intimal surface of the prosthesis by reaction with a compound selected from the group consisting of albumin, glyoxals, ethoxyformic anhydride, formic acid, 1-ethyl-3-(3-dimethylaminopropyl) carbodiimide and the like. The surface charge is then stabilized by treatment with glutaraldehyde, dialdehyde starch, formalin or the like.

22 Claims, 4 Drawing Figures

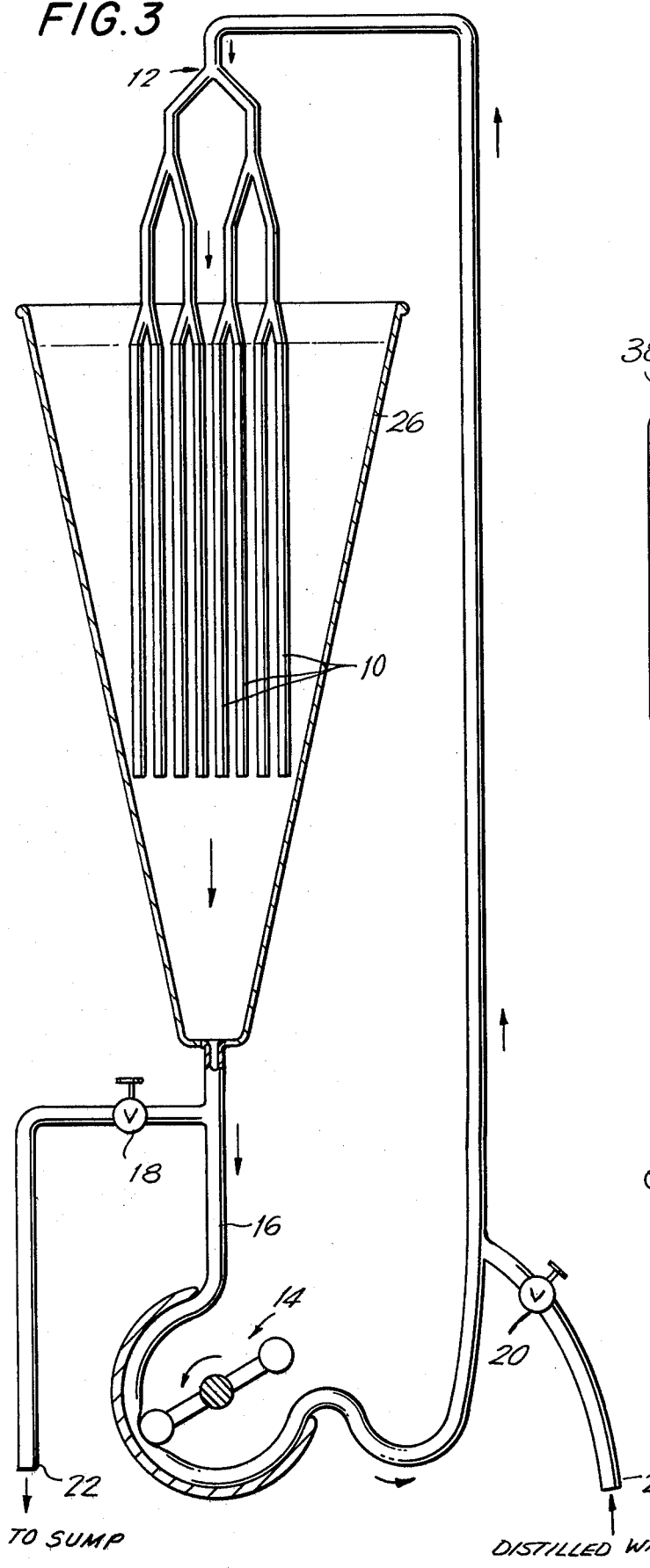
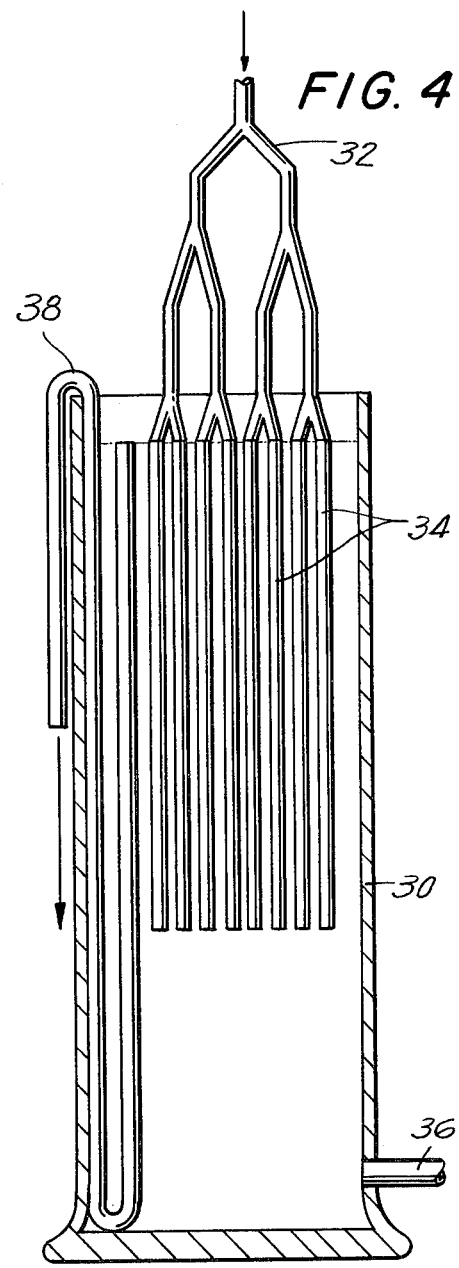

PROSTHESIS AND METHOD FOR MAKING THE SAME

BACKGROUND OF THE INVENTION

1. Field of the Invention

This invention relates to a method for controlling the thrombogenicity of vascular graft prostheses and relates, more particularly, to a method for controlling the thrombogenicity of vascular graft prostheses by rendering the surface charge of the internal surfaces of prostheses more negative or more positive in instances where clotting is sought to be reduced or increased.

2. Description of the Prior Art

It is known to prepare vascular graft prostheses from collagen materials. Such prostheses are in fact available commercially from Johnson and Johnson of New Brunswick, N.J. Pertinent material will be found in the following publications:

Wesolowski, S. A.: The healing of Vascular prostheses, Surgery 57:319, 1965.

Wesolowski, S. A.: Fries, C. C., Domingo, R. T., Fox, L. M. and Sawyer, P. N.: Fate of simple and compound arterial prostheses: Experimental and human observations. In: Fundamentals of Vascular Grafting. McGraw-Hill, New York, 1963, pp. 252-268.

Wesolowski, S. A.: Hennigar, G. R., Rox, L. M., Fries, C. C., and Sauvage, L. R.: Factors contributing to long term failure in human vascular prosthetic grafts. Presented at Symposium on Late Results of Arterial Reconstruction. International Cardiovascular Society Meeting, Rome, September, 1963. J. Cardiov. Surg. 5:44 1964.

Sawyer, P. N., and Pate, J. W.: A study of electrical potential differences across the normal aorta and aortic grafts of dogs. Research Report NM 007081, 10.06. Naval Medical Research Institute, Bethesda, Md., 1953.

Sawyer, P. N., and Pate, J. W.: Bioelectric phenomena as etiologic factors in intravascular thrombosis. Amer. J. Physiol. 175:103, 1953.

Williams, R. D., and Carey, L. C.: Studies in the production of standard venous thrombosis. Ann. Surg. 149:381, 1959.

Schwartz, S. I., and Robinson, J. W.: Prevention of thrombosis with the use of a negative electric current. Surg. Forum 12:46, 1961.

Sadd, J. R., Koepke, D. E., Daggett, R. L., Zarnsdorff, W. C., Young, W. P., and Gott, V. L.: Relative ability of different conductive surfaces to repel clot formation on intravascular prostheses. Surg. Forum 12:252, 1961.

Means, G. E., and Feeney, R. E.: Chemical Modification of Proteins, Holden-Day, Inc., San Francisco, Calif. 1971, pp. 144-148.

SUMMARY OF THE INVENTION

It is an object of the invention to provide an improved method for preparing a vascular graft prosthesis.

Another object of the invention is to provide an improved method for preparing a vascular graft prosthesis which is subject to thrombogenicity in either a reduced or increased degree.

Still another object of the invention is to provide an improved vascular graft prosthesis which is subject to thrombogenicity in either a reduced or increased degree.

These and other objects of the invention are achieved by providing a method, in accordance with the invention, for rendering the surface charge of the intimal surface of the prosthesis more negative or more positive. When reduced thrombogenicity is desired, the surface charge of the intimal surface of the prosthesis is rendered more negative. On the other hand, where increased thrombogenicity is desired, the intimal surface of said prosthesis is rendered more positive.

In its preferred aspects, the method of the present invention for improving the performance of a graft prosthesis by controlling thrombogenicity comprises making a prosthesis from a material selected from the group consisting of (a) collagen and (b) collagen prepared from ficin digested chemically modified artery and vein material and controlling the surface charge of the intimal surfaces of said prosthesis by reaction with a compound selected from the group consisting of albumin, glyoxals, ethoxyformic anhydride, formic acid, 1-ethyl-3-(3-dimethylaminopropyl) carbodiimide and the like.

Insofar as a succinylation reaction is concerned, U.S. Pat. No. 3,927,422 discloses subjecting a tubular collagen vascular graft prosthesis to treatment with succinic anhydride in a basic solution so that its intimal surface has an increased net negative surface charge which prevents thrombosis. As disclosed in U.S. Pat. No. 3,927,422, the graft is generally provided in the form of a collagen tube, one end of which is closed and inserted into a fluid such as ethanol, with a liquid chemical reactant being inserted into the lumen of the tube to increase the negative surface charge of the intimal surface thereof. This reactant, according to said patent, is succinic anhydride in a basic solution. As is also disclosed in the aforementioned U.S. Pat. No. 3,927,422, for carrying out the succinylation reaction, in a typical exemplification, a $NaHCO_3$ buffer solution is injected into the lumen in sequential additions of approximately 10 ml. aliquote to which about 0.1 grams of crystals of succinic anhydride are respectively added. The subject matter of U.S. Pat. No. 3,927,422 is incorporated herein by reference in its entirety.

Insofar as the reaction is concerned, the graft, formed of collagen or collagen prepared from ficin-digested chemically modified artery and vein material or the like, is subjected to reaction with one or more compounds to block or otherwise control the charge of amino acids present, these amino acids including arginine, lysine, hydroxylycine and histidine. A positive charge is rendered more negative by blocking amino acids, as more fully hereinafter described. In this respect, a collagen vessel, chemically modified to neutralize positive charges of basic amino acids, such as those mentioned above, show an increase in the net negative charge on the intimal surface. The surface is then subsequently subjected to tanning with glutaraldehyde or the other tanning compounds to stabilize the net negative charge, while increasing the strength of the prosthesis through cross-linkage. Suitable modifying agents include succinic anhydride, ethoxyformic anhydride, formic acid, albumin, and phenylglyoxal. Another modifying agent useful for neutralizing surface charges in the collagen helix is 1-ethyl-3-(3-dimethylaminopropyl) carbodiimide (also known as EDC).

Prosthesis, treated and tanned, as indicated above, were implanted in mongrel dogs at the carotid and femoral positions. Dogs were sacrificed after implantation periods of two hours, two weeks, one month and three months and studies were also made at one second after implantation. At removal, gross evaluation of the vessels' integrity and thrombogenicity were recorded and the vessels preserved in formalin for histologic studies of each prosthesis and adjacent position of the recipient artery. Marked increases in negative charges or neutralization of the positive charges of basic amino acids were observed.

In its preferred forms, the prosthesis is formed as a vascular prosthesis or as a valve. Preferably the collagen is prepared from ficin digested bovine artery and vein material or the like.

BRIEF DESCRIPTION OF DRAWINGS

FIG. 3 diagrammatically illustrates a form of the apparatus of the invention; and FIG. 4 illustrates a modification of FIG. 3.

DETAILED DESCRIPTION OF DRAWINGS

Figure 1:
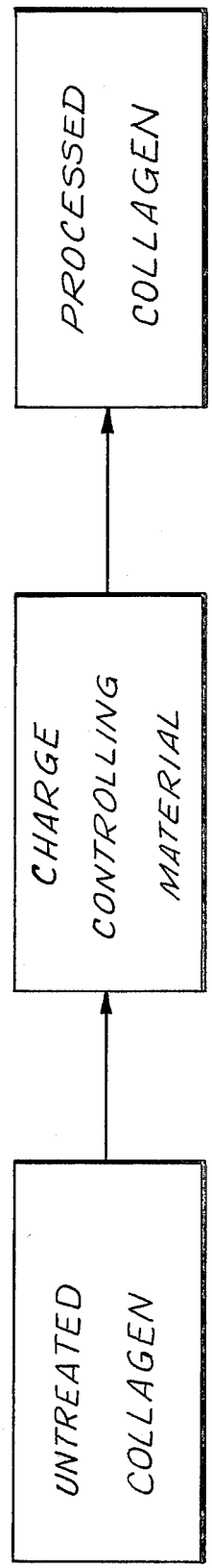
FIG. 1 diagrammatically illustrates the method for practicing the present invention.

It will be noted in FIG. 1 that the untreated collagen of stage 10 is subjected to treatment with a positive or negative charge modifying agent in stage 11 to obtain improved collagen material having increased negative or increased positive surface charge in stage 12.

Figure 2:
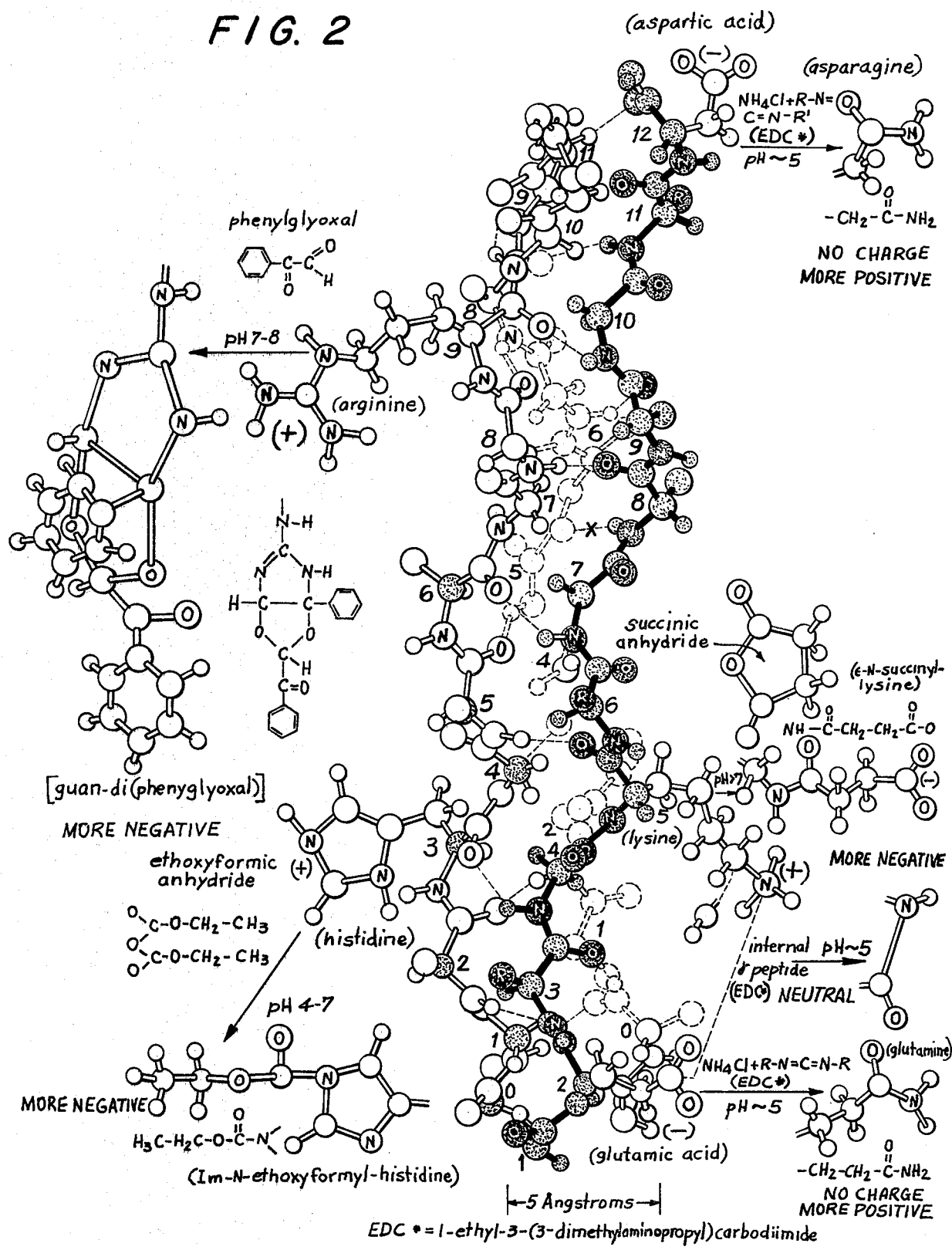
FIG. 2 shows the collagen helix and the applicability of negative or positive charge treating agents according to the theory in which it is believed the improvement is carried out.

FIG. 2 illustrates the improved results obtained employing respective examples of the hereinabove mentioned reactants for modifying the negative or positive surface charge of the internal surfaces of a prosthesis by modifying the positive or negative charge of amino acids present. Tanning by glutaraldehyde and the like stabilizes the charge.

The glutaraldehyde and modifying reactions are indicated below:

(I) Glutaraldehyde cross-linking

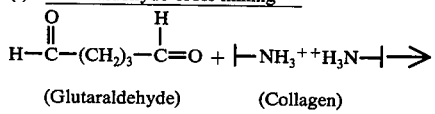
(Glutaraldehyde)  (Collagen)

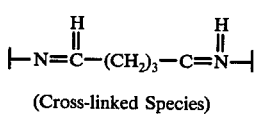
(Cross-linked Species)

(II) Succinylation

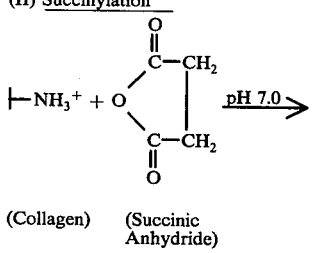
(Collagen) (Succinic Anhydride)

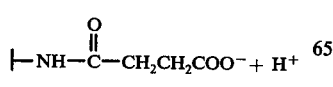
(Collagen - Succinate Linkage)

(III) Albumination

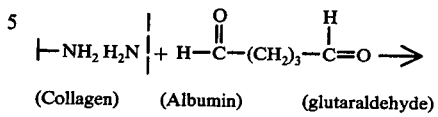
(Collagen) (Albumin) (glutaraldehyde)

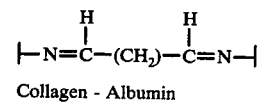
Collagen - Albumin (IV) Arginine Complexing

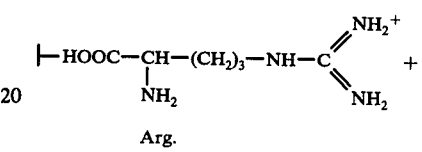
Arg.

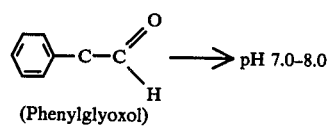
(Phenylglyoxol)

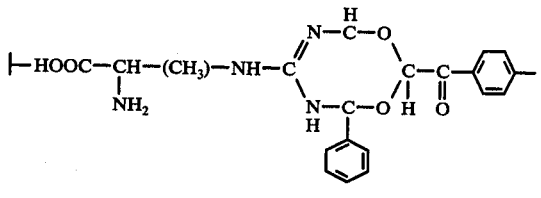
Arg. - Phenylglyoxal Complex (V) Histidine Complexing

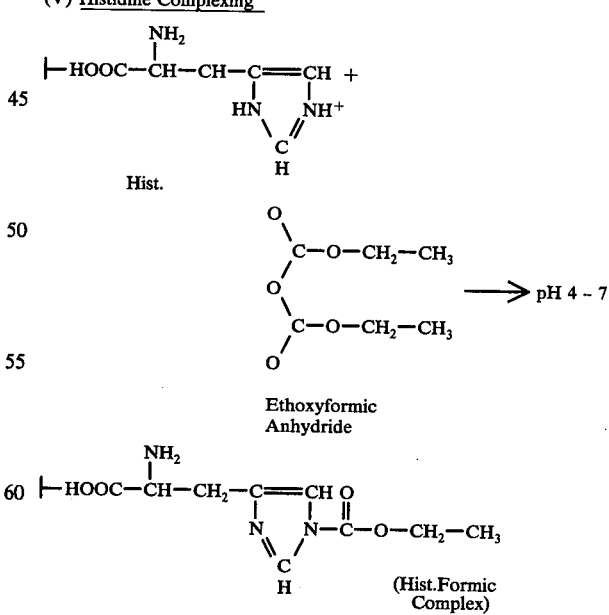

(VI) Lysine Complexing

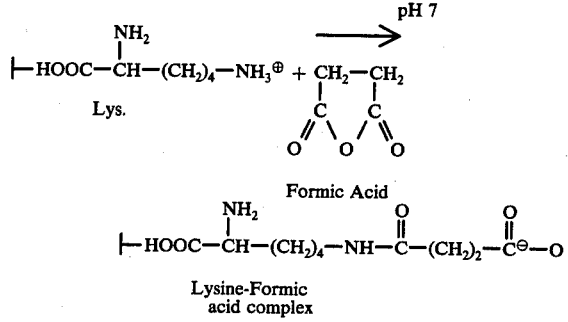

Experimental studies relating to transplantation of modified collagen prostheses have shown that high porosity and net negative intimal surface charge decrease thrombogenicity of vascular grafts. Bovine carotid arteries, which are significantly porous, are, for example, digested by ficin removing muscle and elastin to limit possible reaction. The vessels are then chemically modified to block the positive charges of the amino acids including arginine, lysine, hydroxylysine and histidine to increase the net negative charge on the intimal surface, or to neutralize the aspartic acid and/or glutamic acid to increase the positive charge. Subsequent tanning with glutaraldehyde or the like further stabilized the surface charge while increasing strength through cross-linkages. These prostheses were then implanted in mongrel dogs at the carotid and femoral positions. Studies were made at one second and the dogs were sacrificed after implantation periods of two hours, two weeks, one month and three months. At removal, gross evaluations of the vessels' integrity and thrombogenicity were recorded and the vessels preserved in formalin for histologic studies of each prosthesis and adjacent portions of the recipient artery. Desired tanning, indicative of reduction in thrombogenicity, were observed in each instance.

The following are examples of processes of the invention:

EXAMPLE 1

Arginine Modification

A 2% solution of phenylglyoxal monohydrate (PG) was prepared as follows: 2 g. of PG were first dissolved in 5 ccs. of 95% ethanol. This solution was then added to enough 10% sodium bicarbonate buffer solution (100 g/l.) to make a total of 100 ccs. (ph of the bicarbonate solution was 8.0). Vessels, previously digested by the protease ficin, were then immersed in the PG solution fo 24 hours. The solution was stirred continuously during that period by magnetic stirring rods to insure proper exposure of the full lengths of the vessels to the PG.

After 24 hours, the vessels were washed thoroughly of the PG solution with triple-distilled water (pH of the solution after the reagent had run for 24 hours was 8.3). The vessels were then tanned as follows: Vessels were immersed in 97 ccs. of 10% sodium bicarbonate solution, 3 ccs. of 50% glutaraldehyde solution (3 ccs. of 50% glutaraldehyde/100 ccs. solution). The solution was stirred for 2 hours. Stirring was then discontinued and the vessels were allowed to stand in the tanning solution for 72 hours. After that period, the vessels were washed thoroughly with triple-distilled water and stored in 30%-50% ethanol until implantation.

EXAMPLE 2

Lysine, Hydroxylysine and Arginine Modification

A different group of vessels, previously ficin-digested, glutaraldehyde-tanned and succinylated (with succinic anhydride, for modification of lysine and hydroxylysine residues), were then treated with 2% phenylglyoxal solution (for arginine modification) as described above, and again tanned with glutaraldehyde. The vessels were washed and stored in 30%-50% ethanol until implantation.

EXAMPLE 3

Histidine Modification (Partially Tanned)

Ficin-digested vessels were immersed in a 2% solution of ethoxyformic anhydride, prepared by adding 2 ccs. of ethoxyformic anhydride to enough 30%-50% ethanol to make a total of 100 ccs. of solution. Vessels were left in the solution for 24 hours, during which time it was stirred continuously. After 24 hours, the vessels were washed thoroughly with triple-distilled water, then immersed in a 1.5% glutaraldehyde solution for 72 hours for tanning (as described above).

However, after 72 hours, it was observed that the vessels had not responded to the glutaraldehyde tanning, i.e., they did not show the stiffening and orange-tan color characteristic of tanned vessels. The tanning procedure was therefore repeated for the following 24 hours. Still the vessels did not appear tanned. The vessels were then immersed in a 10% glutaraldehyde solution (as compared to the 1.5% solution used previously) and left there for 24 hours. Tanning was observed after this procedure and it was decided to implant these vessels as they were in this state. They were washed with triple-distilled water and stored in 30%-50% ethanol until implantation. The reason for the inability to tan completely these vessels are speculative. It is believed that in some way, the ethoxyformic anhydride blocked the $NH_3^+$ groups of these amino acid residues normally involved in the tanning process from reacting with the glutaraldehyde.

EXAMPLE 4

Lysine, Hydroxylysine, Arginine and Histitine Modification

A fifth group of vessels, previously treated with succinic anhydride (lysine and hydroxylysine modification), tanned with glutaraldehyde, then again succinated, were then subjected to arginine and histidine modification by treatment first with phenylglyoxal for 24 hours (arginine) and then with ethoxyformic anhydride for 24 hours (histidine) by the above described procedures.

EXAMPLE 5

Histidine Modification (Completely Tanned)

Ficin-digested vessels were immersed in a 1.5% glutaraldehyde and 10% sodium bicarbonate solution for 24 hours for tanning. After the vessels were washed thoroughly with triple-distilled water, they were immersed in a 2% solution of ethoxyformic anhydride, prepared by adding 2 ccs. of ethoxyformic anhydride to enough 30%-50% ethanol to make a total of 100 ccs. of solution. Vessels were left in the solution for 24 hours, during which time it was stirred continuously. After that period, the vessels were washed thoroughly with triple-distilled water and stored in 30%-50% ethanol until implantation.

EXAMPLE 6

Albumin Modification

Vessels, digested with ficin, were washed with distilled water and immersed in 10% sodium becarbonate (100 gm/l.) for ½ hour. A solution of 10% sodium bicarbonate (100 mg/l.) and 3% bovine or human albumin (25 gm/l.) was prepared. The vessels were placed into the solution for a period of three hours. Glutaraldehyde [1.5% (15 gm/l.)] was added dropwise with stirring to the above solution and left in the refrigerator for at least 24 hours to allow for complete exposure of all vessel surface to the tanning agent. The vessels were then removed from the tanning agent. The vessels were then removed from the tanning solution, succinated for 3 hours, and placed in 30-50% EtOH until implantation or further modification.

Operational Technique

An oblique incision was made in the skin along the anterior border of the sternocleidomastoid muscle. The jugular vein was exposed by dissecting it free of its surrounding superficial and deep cervical fascia were incised. Moderate bleeding was controlled with direct pressure. The sternomastoid muscle was retracted posteriorly to expose the carotid sheath. The carotid sheath was opened by blunt dissection and the carotid artery was then separated from the vagus nerve and an accompanying vein for a length of 10 cms.

Femoral artery and Vein Dissection

An incision, beginning at the inguinal ligament and continuing caudad (10 cms.) along the medial aspect of the thigh, was made to expose the superficial femoral fascia and the underlying femoral sheath. Upon dissection of the superficial femoral fascia, the femoral artery and vein are seen to lie within the femoral sheath. These vessels were then dissected free of the sheath and the branches of the femoral artery (superficial circumflex iliac artery, external pudendal artery, medial and lateral femoral circumflex arteries) were identified. The section of vessel to receive the implant was chosen by the criterion of having the smallest number of branches along a 5 cms. length of the vessel. Small branches were ligated with 2-0 silk near their origin and termination and divided between the two ties.

Preparation and implantation of vessels (acute)

Collagen vessels were removed from alcohol prior to implantation; dacron and teflon (P.T.F.E.) grafts were removed from their respective containers. Grafts were then cut to the desired length (30 mms.) mounted over HCl-cleaned stainless steel cannulas and tied to the cannulas with umbilical tapes. They were then washed thoroughly in sterile water and placed in saline until implantation.

Both arteries and veins in the neck and femoral regions received acute implants. The vessel was clamped with long vascular clamps or bulldog clamps at two points approximately 7 cms. apart. A third clamp was placed midway between the first two using fine curved vascular scissors. A transverse incision was made on either side of the middle clamp through one wall of the vessel. Grafts were then removed from sterile saline, inserted by their free cannula ends into the 'slits' in the vessel and secured by umbilical tapes. The blood vessel was then severed and the middle clamp removed. The vascular clamps were then removed (clamp distal to blood flow removed first) and blood flow was permitted through the graft for the required time period, either 1 second or 2 hours. After the graft was exposed to blood flow for the required period, the vessel was again clamped and the graft removed and placed immediately in formalin.

Preparation and implantation of vessels (chronic)

Collagen vessels were removed from alcohol prior to implantation, cut to the desired length (approx. 30 mms.) and washed thoroughly in sterile saline. Dacron and teflon (P.T.F.E.) grafts were cut to the desired length (30 mms.) and sterilized.

Only arteries in the neck, femoral regions and abdominal aorta received chronic implants. The selected artery was clamped with long vascular or bulldog clamps at two points approximately 7 cms. apart. The artery was then severed midway between the two clamps with fine curved vascular scissors. The graft was sutured at either end to the artery with a continuous stitch using 5-0 or 6-0 monofilament nylon sutures. After the clamps were removed and any major bleeding areas along the suture line repaired, measurements were made of the outside diameter of the graft, the outside diameter of the artery, and the length of the graft. The surgical wound area was then irrigated with Kantrex (Kanomycin) solution (0.4%), and fascia and skin were each sutured with 2-0 silk. In each instance, control of reduced thrombogenicity was observed.

Although a stirring type technique has been described above, a more preferred technique for making negatively or positively charged collagen prosthesis involves a recirculation system as shown in FIG. 3 in which the bovine heterografts 10 with side branches tied off are placed on a multi-limbed perfusion "Christmas tree" 12. The ficin and other despeciating or charging solutions are pumped by pump 14 in a continuous circuit 16 through this system so that all the surface of the calf carotid arteries are perfused on a continuing basis. In this way, all of the internal surfaces of the grafts are equally processed by constant flow over their surfaces of the reacting solution.

In addition to this recirculating chemical reactant system, there are included two valve systems 18 and 20 which permit bleeding off the reactive solutions at 22 and providing irrigations at 24 with distilled water from the Cullegan dionizing system. The inverted conical vessel 26 is employed to accumulate the solution to bathe the outer surfaces of the grafts. Through the interior of each of the grafts the solution preferably flows at a rate of 50±25 ccs. per minute or 1 volume through each graft per minute.

FIG. 4 shows the substitution of a cylindrical vessel 30 using Christmas tree arrangement 32 supporting grafts 34. The flush is provided at 36 and the solution 13 is drawn out at 38. The following relate to the processes previously indicated:

I. Glutaraldehyde covalently bonds with collagen to product successful cross linking as shown and produces a ± increase in negative charge. It had one interesting problem, the excessive gluteraldyhyde on the surface must be neutralized in some fashion so that it will not react with blood and cause instantaneous thrombosis at the time of exposure of the graft inner surface to blood.

II. Succinilation produces a maximum negative charge cross linking with most available NH3 groups on the exposed lycine side chains of the collagen helix.

III. Albuminization apparently has less specificity but is more effective having a covering capacity combining with almost all available NH3 groups, producing a surface mono layer of albumin which in this instance is cross linked to the underlying helix by glutaraldehyde as shown, producing a collagen albumin bond and a double bond with glutaraldehyde with a very tight covalent bonding.

IV. Phenylglyoxal combines with arginine on the heavy chain of the collagen helix as shown in FIG. 2 and as shown as chemical equation where the arganine has an exposed $$C\!\!\begin{array}{c}\nearrow NH_{2+}\\ \searrow NH_{2+}\end{array}$$

cross linking occurring with the NH2 losing one hydrogen atom and attaching to the carboxyl group of phenylglyoxal as shown. This produces a (3−) negative charge.

V. With histidine, ethoxyformic anhydride complexing occurs in much the same way as arginine combines with succinicanhydride and produces a moderate negative charge.

VI. Lysine combines with formic acid to form a lysineformic acid complex.

Actually, it is possible to sequentially cross link the collagen with these various materials to produce a highly negatively charged collagen linkage.

Although the present invention has been described with preferred embodiments, it will be understood that various modifications and adaptations thereof may be resorted to without departing from the spirit and scope of the invention, as those skilled in the art will readily understand.

What is claimed is:

1. A method for controlling thrombogenicity of a graft prosthesis comprising making a prosthesis selected from the group consisting of (a) collagen and (b) collagen prepared from ficin digested chemically modified artery or vein material and controlling the surface charge of the intimal surfaces of said prosthesis by reaction with a solution of a compound selected from the group consisting of bovine or human albumin, succinic anhydride, glyoxals, formic acid, ethoxyformic anhydride and 1-ethyl-3-(3-dimethylaminopropyl) carbodiimide.

2. A method as claimed in claim 1 comprising stabilizing the surface charge by administering a stabilizing agent.

3. A method as claimed in claim 2 wherein the stabilizing agent is selected from the group consisting of glutaraldehyde, dialdehyde starch or formalin.

4. A method as defined in claim 1 wherein the collagen is prepared from ficin digested bovine carotid artery material.

5. A method as defined in claim 1 wherein the prosthesis is formed as a vascular prosthesis.

6. A method as defined in claim 1 wherein the prosthesis is formed as a cardiac valve.

7. A method as defined in claim 1 wherein the graft prosthesis includes amino acids selected from the group consisting of arginine, lysine, hydroxylysine and histidine.

8. A prosthesis made as defined in claim 1.

9. A method as defined in claim 1 wherein the collagen is dialdehyde starch tanned collagen.

10. A method for controlling thrombogenicity of a graft prosthesis comprising making a prosthesis of a collagen, increasing the negative surface charge of said prosthesis and stabilizing the surface charge by a glutaraldehyde reaction according to the following chemical reaction:

$$H-\overset{O}{\overset{\|}{C}}-(CH_2)_3-\overset{H}{\overset{|}{C}}\!=\!O + \vdash\!\!-NH_3+$$
$$+H_3N\!\!-\!\!\vdash\!\!\longrightarrow\!\!\rangle\!\!-N\!=\!\overset{H}{\overset{|}{C}}-(CH_2)_3-\overset{H}{\overset{|}{C}}\!=\!N\!\!-\!\!\dashv.$$

11. A method for decreasing the thrombogenicity of a vascular graft prosthesis comprising rendering the surface charge of the internal surface of said prosthesis more negative.

12. A method for increasing the thrombogenicity of a vascular graft prosthesis comprising rendering the surface charge of the internal surface of said prosthesis more positive.

13. A method as defined in claim 11 wherein said prosthesis has on the internal surface thereof compounds exhibiting a positive charge comprising rendering said positive charge more negative by blocking said compounds.

14. A method as defined in claim 13 wherein said compounds comprise at least one compound selected from the group consisting of arginine, lysine, hydroxylysine and histidine.

15. A method as defined in claim 1 wherein the surface charge is controlled by bovine or human albumin.

16. A method as defined in claim 1 wherein the surface charge of the internal surfaces of said prosthesis is controlled by reaction with glyoxals.

17. A method as defined in claim 1 wherein the surface charge of the internal surfaces of said prosthesis is controlled by reaction with ethoxyformic anhydride.

18. A method as defined in claim 1 wherein the surface charge of the internal surfaces of said prosthesis is controlled by reaction with 1-ethyl-3-(3-dimethylamino propyl)carbodiimide.

19. A method as claimed in claim 1 wherein said prosthesis is a tube, comprising closing off an end of said tube, inserting said solution into said tube, and stirring said solution.

20. A method as claimed in claim 1 comprising flowing said solution through said tube.

21. A method as claimed in claim 20 wherein said solution flows through the tube at a rate of 50 ± cc. per minute.

22. A method as claimed in claim 20 wherein said solution flows through the tube at a rate of one volume ± 20% per minute.

* * * * *